(12) United States Patent
Nakatsuka et al.

(10) Patent No.: US 7,344,658 B2
(45) Date of Patent: Mar. 18, 2008

(54) RADIATION PROTECTOR AND UTILIZATION THEREOF

(75) Inventors: Hirosige Nakatsuka, Himeji (JP); Akihito Tsuchiya, Shiga (JP); Quang Huy Nguyen, Shiga (JP)

(73) Assignee: Allmighty Co., Ltd., Hyogo (JP)

( * ) Notice: Subject to any disclaimer, the term of this patent is extended or adjusted under 35 U.S.C. 154(b) by 0 days.

(21) Appl. No.: 10/502,511

(22) PCT Filed: Jan. 23, 2003

(86) PCT No.: PCT/JP03/00588

§ 371 (c)(1),
(2), (4) Date: Jul. 23, 2004

(87) PCT Pub. No.: WO03/063179

PCT Pub. Date: Jul. 31, 2003

(65) Prior Publication Data

US 2005/0087705 A1  Apr. 28, 2005

(30) Foreign Application Priority Data

Jan. 23, 2002 (JP) .............................. 2002-014868

(51) Int. Cl.
  *G21F 1/00* (2006.01)
  *G21F 1/10* (2006.01)
  *G21F 1/12* (2006.01)
  *A61K 8/30* (2006.01)
  *A61K 8/65* (2006.01)

(52) U.S. Cl. .................. 252/478; 250/515.1; 250/516.1; 523/135; 523/137; 524/21; 524/22

(58) Field of Classification Search .................. 252/478
See application file for complete search history.

(56) References Cited

U.S. PATENT DOCUMENTS

| | | | | |
|---|---|---|---|---|
| 3,808,113 | A * | 4/1974 | Okamura et al. | 427/493 |
| 4,638,024 | A * | 1/1987 | Sato et al. | 524/22 |
| 4,946,450 | A * | 8/1990 | Erwin | 604/294 |
| 5,587,411 | A * | 12/1996 | Sakaki et al. | 524/17 |
| 5,718,954 | A * | 2/1998 | Sano et al. | 428/35.6 |
| 7,041,994 | B2 | 5/2006 | Hayashi et al. | |
| 2002/0197296 | A1* | 12/2002 | Gen | 424/423 |
| 2003/0003157 | A1* | 1/2003 | Ohan et al. | 424/499 |
| 2003/0091518 | A1* | 5/2003 | Pauly et al. | 424/59 |
| 2003/0091646 | A1* | 5/2003 | Gen | 424/486 |
| 2007/0128246 | A1* | 6/2007 | Hossainy et al. | 424/423 |

FOREIGN PATENT DOCUMENTS

| | | |
|---|---|---|
| EP | 0 379 409 A | 7/1990 |
| EP | 1020874 A1 * | 7/2000 |
| GB | 2092444 A | 8/1982 |
| GB | 2227410 A | 8/1990 |
| JP | 01-280465 | 11/1989 |
| JP | 09-241399 | 9/1997 |
| JP | 10-338615 | 12/1998 |
| WO | WO 99/17303 | 9/1997 |
| WO | WO 98/55075 | 10/1998 |
| WO | WO 01/45661 A2 | 12/2000 |

OTHER PUBLICATIONS

USPTO obtained translation of JP 10-338615 (Urita, Shoji) (Dec. 22, 1998).*
USPTO obtained translation of JP 01-280465 (Natsume, et al.) (Nov. 10, 1989).*
USPTO obtained translation of JP 9-241399A.*
Talty, J. T., "Industrial Hygiene Engineering—Recognition, Measurement, Evaluation and Control (2nd Edition)," (1998, William Andrew Publishing/Noyes) p. 621-647, 659-698.*
Slavato, Joseph A., "Environmental Engineering and Sanitation (Fourth Edition)," (1992, John Wiley & Sons, Inc, New York) p. 846-897.*
Pfafflin et al., "Encyclopedia of Environmental Science and Engineering (Fourth Edition)," (1998, Gordon and Breach Science Publishers, The Netherlands) p. 1109.*
Abstract of WO 95/17157A2 (Jun. 29, 1995).*
DATABASE WPI Section Ch, Week 197749 Derwent Publications Ltd., London, GB; Class A97, AN 1977-87784&, XP002368977 & SU 500 735 A (Levenko, P.I.) May 30, 1977, Abstract.
DATABASE WPI, Section Ch, Week 198746, Derwent Publications Ltd., London, GB; Class A96, AN 1987-325961, XP002369026 & RO 91 724 A (Inst. Cont. Stat. Med.) May 30, 1987, Abstract.
Supplementary European Search Report from corresponding European Patent Application Serial No. EP 03 70 1847, Feb. 21, 2006.

* cited by examiner

*Primary Examiner*—Joseph D. Anthony
(74) *Attorney, Agent, or Firm*—Knobbe, Martens, Olson & Bear, LLP

(57) ABSTRACT

The present invention provides radioprotective materials and products produced using the materials, the materials and products being easily usable for blocking the effects of radiation, exposure to which occurs unconsciously in daily life or in the working environment. Specifically stated, the present invention provides radioprotective materials comprising at least one member selected from the group consisting of collagens, keratins, silk fibroins and their derivatives. The present invention also provides radioprotective products produced using the radioprotective materials.

3 Claims, No Drawings

RADIATION PROTECTOR AND UTILIZATION THEREOF

This application is the U.S. National Phase under 35 U.S.C. §371 of International Application PCT/JP03/00588, filed Jan. 23, 2003, which claims priority to JP 2002-14868, filed Jan. 23, 2002.

TECHNICAL FIELD

The present invention relates to materials capable of reducing the adverse effects of radiation, i.e., radioprotective materials. The present invention also relates to products having radioprotective effects owing to the radioprotective materials contained therein. The present invention further relates to methods for blocking or reducing the adverse effects of radiation exposure.

BACKGROUND ART

In recent years, increasing amounts of radioactive wastes are being generated from nuclear power facilities such as nuclear power plants, as well as medical facilities, universities and laboratories that use radioisotopes. Accordingly, reliable measures for radioprotection against the radioactive wastes are demanded.

Further, it is said that miners in uranium ore, coal and metal mines are exposed to more than 6 times as much radiation from the earth's crust as allowed by international recommendations for radiation workers. Moreover, the amount of radiation from outer space (cosmic rays) to which flight crews are exposed is said to be even greater than that to which miners are exposed. Solutions to the problems of radiation exposure in such environments are urgently required.

Besides the specific sources mentioned above, luminous paints on clock or watch faces, glow lamps in fluorescent lamp devices, discharge tubes in displays in gas stations and the like, and smoke detectors in buildings employ isotopes that emit alpha or beta rays. Therefore, proper radiation control is always necessary in sites producing these items.

Thus, with recent industrial development, people are exposed to not only natural radiation such as ultraviolet rays, but also artificial radiation, in daily life and the working environment. Therefore, effective protection of the body from such radiation is required.

To protect internal or external parts of the body (such as the skin, hair, eyes or the like) from ultraviolet rays, one type of radiation, sunglasses with large light-colored lenses, hats with all-round brims with a width of at least 7 cm, dark-colored clothes made of polyester or hemp fibers, and ultraviolet-blocking cosmetics containing titanium oxide are reportedly effective. However, these means block only Ultraviolet-B, which damages DNA in the epidermis of the body, promotes the formation of melanin pigment, rapidly increases active oxygen and thereby ages the tissue cells of the epidermis, and causes skin spots. It is known that Ultraviolet-A penetrates deep into the dermis of the body and cuts or destroys elastic fibers to thereby form unremovable wrinkles or cause cataracts. Further, the recent depletion of the ozone layer allows a large amount of Ultraviolet-C to reach the earth, and thus the effects of Ultraviolet-C pose problems. Thus, protective means against Ultraviolet-A and Ultraviolet-C, in addition to those against Ultraviolet-B, are hoped for.

Moreover, exposure to alpha rays, beta rays, X-rays, gamma rays or like ionizing radiation which penetrates into the human body has not only short-term effects, known as acute disorders, on the human body including the blood and organs, but also long-term effects such as carcinogenesis, genetic damage and the like.

The development of a protective material against the radiation is desired in order to ensure radioprotection of people in general, not just workers in environments where radiation exposure is likely to occur.

DISCLOSURE OF THE INVENTION

An object of the present invention is to provide an easily usable radioprotective material for blocking the adverse effects of radiation, exposure to which occurs or is likely to occur inevitably, unconsciously and/or accidentally in daily life or the working environment, and for protecting a subject from exposure to such radiation. Another object of the invention is to provide a method for reducing the adverse effects of various types of radiation on a subject by using the radioprotective material.

The present inventors carried out extensive research to achieve the above objects. As a result, the inventors found that collagens, keratins, silk fibroins and their derivatives are capable of blocking or reducing the adverse effects of various types of radiation. Further, we confirmed that the use of this characteristic of the above substances makes it possible to protect organisms or articles from inevitable and/or unconscious radiation exposure that may occur in daily life or the working environment. The present invention has been accomplished based on these findings.

The present invention provides the following:

1. A radioprotective material comprising at least one member selected from the group consisting of collagens, keratins, silk fibroins and their derivatives.

2. A radioprotective material comprising at least one member selected from the group consisting of collagens and their derivatives.

3. A radioprotective material according to item 1, which provides protection from at least one member selected from the group consisting of cosmic rays, radio waves, electromagnetic waves, infrared rays, visible light, ultraviolet rays, alpha rays, beta rays, proton beams, baryon beams, X-rays, gamma rays, electron beams and neutron beams.

4. A radioprotective material according to item 1, which provides protection from at least one member selected from the group consisting of cosmic rays, electromagnetic waves, Ultraviolet-A, Ultraviolet-B, alpha rays, beta rays, proton beams, baryon beams, X-rays, gamma rays, electron beams and neutron beams.

5. A radioprotective product comprising a radioprotective material according to item 1.

6. A radioprotective product according to item 5, comprising 0.05 wt. % to 40 wt. % in total of at least one member selected from the group consisting of collagens, keratins, silk fibroins and their derivatives.

7. A radioprotective product according to item 6, which is at least one member selected from the group consisting of radioprotective plastic product, radioprotective film, radioprotective sheet, radioprotective coating agent, radioprotective cosmetic product, radioprotective fiber and radioprotective preparation.

8. A radiation-resistant medical or experimental material, comprising a radioprotective material according to item 1.

9. A radiation-resistant medical or experimental material, comprising a radioprotective product according to item 5.

10. Use as a radioprotective material of at least one member selected from the group consisting of collagens, keratins, silk fibroins and their derivatives.

11. Use for the production of a radioprotective material of at least one member selected from the group consisting of collagens, keratins, silk fibroins and their derivatives.

12. Use for the production of a radioprotective product of at least one member selected from the group consisting of collagens, keratins, silk fibroins and their derivatives.

13. A method for blocking or reducing the adverse effects of radiation on a subject, the method comprising protecting a subject with a radioprotective material according to item 1.

14. A method according to item 13, wherein at least one member selected from the group consisting of collagens, keratins, silk fibroins and their derivatives is administered to, mixed with, coated on or immobilized on a subject.

15. A method according to item 13, wherein a product comprising at least one member selected from the group consisting of collagens, keratins, silk fibroins and their derivatives is used to protect a subject.

16. A method according to item 15, wherein a product comprising at least one member selected from the group consisting of collagens, keratins, silk fibroins and their derivatives is placed over, applied to or administered to a subject.

17. A method according to item 13, wherein at least one member selected from the group consisting of collagens, keratins, silk fibroins and their derivatives is used in such a manner that the at least one member is present inside a subject or inside a surface layer of the subject in a total amount of 0.05 wt. % to 40 wt. %.

In this specification and the appended claims, the term "radioprotective material" means a material capable of blocking or reducing the effects of radiation on a subject. The term "radioprotective product" means a product that has radioprotective capability and that is used for blocking or reducing the effects of radiation on a subject.

BEST MODE FOR CARRYING OUT THE INVENTION (I) Radioprotective Material and Radioprotective Product The radioprotective material of the invention comprises at least one member selected from the group consisting of collagens, keratins, silk fibroins and their derivatives.

In this specification and the appended claims, the term "radiation" is used in a broad sense. Specifically stated, radiation includes cosmic rays, radio waves, electromagnetic waves, infrared rays, visible light, ultraviolet rays (Ultraviolet-A, Ultraviolet-B and Ultraviolet-C), alpha rays, beta rays, proton beams, baryon beams, X-rays, gamma rays, electron beams, neutron beams and the like. Preferably, the types of radiation in the present invention are those against which protection is required, i.e., cosmic rays, electromagnetic waves, Ultraviolet-A, Ultraviolet-B, alpha rays, beta rays, proton beams, baryon beams, X-rays, gamma rays, electron beams and neutron beams.

The types of collagen usable in the present invention are not limited in origin or production process. Examples of collagen sources include skin tissues, cartilage tissues, bone tissues, blood vessel tissues, organs and tendons of animals such as cows, pigs, sheep, humans and other mammals, chickens and other birds, tunas, skipjacks, crucian carps and other fish, squids, octopuses and other mollusks, arthropods, etc. The collagens for use in present invention may be prepared in the standard manner from the tissues of such animals, or may be produced by genetic engineering techniques.

Further, the collagens may be solubilized collagens, such as acid-solubilized collagens, enzyme-solubilized collagens (atelocollagens), alkali-solubilized collagens, or the like.

Moreover, derivatives of these collagens can also be used in the present invention. Examples of collagen derivatives include collagens modified with saccharides such as monosaccharides (e.g., arabinose, xylose, ribose, glucose, galactose, mannose, etc.), oligosaccharides (e.g, cellobiose, maltose, degraded mannan, oligosaccharides containing the above saccharides, etc.), polysaccharides (e.g., cellulose, amylose, mannan, chitin, chitosan, etc.), glucosaminoglucan, chondroitin sulfate or the like; collagens acylated with succinic acid, phthalic acid, acetic acid, fatty acids, compounds containing quaternary ammonium, compounds containing quaternary ammonium and fatty acids, or the like; condensates of fatty acid amines and collagens; collagens esterified with $C_1$ to $C_{20}$ hydrocarbon alcohols such as methyl alcohol, ethyl alcohol, propyl alcohol, isopropyl alcohol, lauryl alcohol, lauroyl alcohol, cetyl alcohol, 2-ethylhexyl alcohol 2-hexyldecyl alcohol and stearyl alcohol; crosslinked collagens; cationized collagens; lauryldimonium hydroxypropyl collagens; stearyldimonium hydroxypropyl collagens; AMP-isostearoyl collagens; and other quaternized collagens.

In the present invention, such collagens and collagen derivatives may be used singly or in combination.

The types of keratin usable in the present invention are not limited in origin or production process, and may be prepared by standard means from horns, hair or other animal parts, or may be produced by genetic engineering techniques. Further, the keratins may be keratins hydrolyzed by the action of acids, enzymes, or the like.

Keratin derivatives can also be used in the present invention. Examples of keratin derivatives include keratins modified with saccharides such as monosaccharides (e.g., arabinose, xylose, ribose, glucose, galactose, mannose, etc.), oligosaccharides (e.g, cellobiose, maltose, degraded mannan, oligosaccharides containing the above saccharides, etc.), polysaccharides (e.g., cellulose, amylose, mannan, chitin, chitosan, etc.), glucosaminoglucan or the like; keratins acylated with succinic acid, phthalic acid, acetic acid, fatty acids, compounds containing quaternary ammonium, compounds containing quaternary ammonium and fatty acids, and the like; condensates of fatty acid amines and keratins; keratins esterified with $C_1$ to $C_{20}$ hydrocarbon alcohols such as methyl alcohol, ethyl alcohol, propyl alcohol, isopropyl alcohol, lauryl alcohol, lauroyl alcohol, cetyl alcohol, 2-ethylhexyl alcohol, 2-hexyldecyl alcohol and stearyl alcohols; cationized keratins; lauryldimonium hydroxypropyl keratins; cocodimonium hydroxypropyl keratins; and keratins modified with other quaternary ammonium-containing compounds.

In the present invention, such keratins and keratin derivatives may be used singly or in combination.

The types of silk fibroin usable in the present invention are not limited in origin or production process. The silk fibroins may be, for example, refined from silk, or may be produced by genetic engineering techniques. The silk fibroins may be silk fibroins hydrolyzed by the action of acids, enzymes or the like.

Silk fibroin derivatives can also be used in the present invention. Examples of silk fibroin derivatives include silk fibroins modified with saccharides such as monosaccharides (e.g., arabinose, xylose, ribose, glucose, galactose, mannose, etc.), oligosaccharides (e.g, cellobiose, maltose, degraded mannan, oligosaccharides containing the above saccharides, etc.), polysaccharides (e.g., cellulose, amylose, mannan, chitin, chitosan, etc.), glucosaminoglucan or the like; silk fibroins acylated with succinic acid, phthalic acid, acetic acid, fatty acids, compounds containing quaternary ammonium, compounds containing quaternary ammonium and fatty acids, or the like; condensates of fatty acid amines and silk fibroins; silk fibroins esterified with $C_1$ to $C_{20}$ hydrocarbon alcohols such as methyl alcohol, ethyl alcohol, propyl alcohol, isopropyl alcohol, lauryl alcohol, lauroyl alcohol, cetyl alcohol, 2-ethylhexyl alcohol, 2-hexyldecyl alcohol and stearyl alcohol; cocodimoniuim hydroxypropyl silk fibroins; silk fibroins modified with polyethylene glycols; silk fibroin derivatives obtained by graft polymerization of polymers or copolymers comprising (meth)acrylic acid type monomers or olefin-type unsaturated monomers.

In the present invention, such silk fibroins and silk fibroin derivatives may be used singly or in combination.

In the radioprotective material of the present invention, such collagens, keratins, silk fibroins and their derivatives may contain salts such as metal salts, sulfonates, phosphonates, hydrochlorides, phosphates and or the like.

The radioprotective material of the present invention comprises at least one member selected from the group consisting of collagens, keratins, silk fibroins, and their derivatives. Preferably, the radioprotective material comprises at least one member selected from the group consisting of collagens and their derivatives.

The collagens, keratins, silk fibroins and their derivatives are capable of effectively blocking the adverse effects of radiation. Thus, the radioprotective material of the present invention may consist only of the at least one member selected from collagens, keratins, silk fibroins and their derivatives, or may contain additives or carriers in addition to these active ingredient substances.

The radioprotective material can be used singly or in combination with other materials to prepare a variety of radioprotective products having radioprotective effects. Examples of such radioprotective products include, but not limited to, a radioprotective plastic product, radioprotective coating agent, radioprotective film, radioprotective sheet, radioprotective cosmetic product, radioprotective fiber and radioprotective preparation.

When the radioprotective material is used in combination with other materials to produce the radioprotective product, the preferred proportion of the radioprotective material in the product cannot be generally defined, since it varies depending on type of the radiation to be blocked, type of the product, intended use of the product, type of the radioprotective material, expected results, and the like. To give an example, however, the product usually contains at least one member selected from the group consisting of collagens, keratins, silk fibroins and their derivatives in a total proportion of about 0.05 wt. % to about 40 wt. %, and preferably about 1 wt. % to about 10 wt. %. If the proportion of these components is markedly lower than 0.05 wt. %, the radioprotective effects are likely to be low. On the other hand, these components, when contained in a proportion higher than 40 wt. %, have no bad influence on the radioprotective effects. Thus, the product may contain more than 40 wt. % of these components as long as molding and processing of the product are not adversely influenced.

The radioprotective plastic product can be produced by, for example, mixing polymers for use in production of plastic products and the radioprotective material, and then subjecting the mixture to hot extrusion, casting, drawing or like process to form films, sheets, blocks, etc. Polymers usable for the production of the product is not limited, but biodegradable polymers are preferable from the viewpoint of ease of disposal and the like. Any biodegradable polymers presently known or developed in the future can be used. Examples of biodegradable polymers presently marketed or experimentally produced include microbial biodegradable plastics available under the tradenames BIPOL (polyhydroxybutylate/hydroxyvalerate copolymer, Japan Monsanto Co., Ltd.) and BIOGREEN (polyhydroxybutylate, Mitsubishi Gas Chemical Co., Inc.) and the like; natural biodegradable plastics available under the tradenames MATER-BI (starch/polylactic acid, The Nippon Synthetic Chemical Industry Co., Ltd.), CORNPOL (modified starch, Nippon Cornstarch), CELGREEN PCA (cellulose acetate, Daicel Chemical Industries, Ltd.) and DOLON CC (chitosan/cellulose/starch, Aicello Chemical Co., Ltd.) and the like; and synthetic biodegradable plastics available under the tradenames LACTEE (polylactic acid, Shimadzu Corp.), LACEA (polylactic acid, Mitsui Chemicals, Inc.), ECOPLA (polylactic acid, Cargil-Dow), CELGREEN (cellulose acetate plastic, Daicel Chemical Industries, Ltd.), CELGREEN P-H, P-HB (polycaprolactone, Daicel Chemical Industries, Ltd.), BIONOLLE (polybutylene succinate, polybutylene succinate/adipate copolymer, Showa Highpolymer Co., Ltd.), YUPEC (polybutylene succinate carbonate, Mitsubishi Gas Chemical Co., Inc.), LUNARE SE (polyethylene succinate, Nippon Shokubai Co., Ltd.) and POVAL (polyvinyl alcohol, Kuraray Co., Ltd.) and the like.

The radioprotective film and radioprotective sheet of the present invention are film and sheet products, respectively, produced using the radioprotective material. Plastic film and sheet are encompassed by the radioprotective plastic products described above. The radioprotective film can be produced using the radioprotective material by, for example, preparing an aqueous suspension containing 0.1 to 10 wt. % of the radioprotective material and then casting the suspension on a smooth surface, followed by evaporation to dryness. The radioprotective sheet can be produced using the radioprotective material, for example, by laminating films obtained by the above process via an aqueous suspension of the radioprotective material or water applied between the films, followed by compression of the laminate to remove the moisture.

The radioprotective plastic product, radioprotective film and radioprotective sheet thus obtained can be used as a packaging material for various articles that are liable to be damaged or otherwise adversely affected by radiation (for example, agricultural products, marine products, foods, precision electronic instruments, etc.). Further, these radioprotective products can also be used, for example, as or as part of building materials, flooring materials, clothing, footwear, curtains, medical materials, aircraft interior materials, components of radiation equipment, laboratory gloves, multi-purpose films for agricultural and stock farming applications, multi-purpose sheets for agricultural and stock farming applications, carrier tapes for IC chip fabrication, etc.

The radioprotective coating agent is a coating agent used for imparting radioprotective properties to products for which radioprotective measures are required. The radioprotective coating agent of the present invention can be prepared using solely the radioprotective material, or where necessary, may be prepared by dissolving the material in a solvent, followed by addition of conventional coating agent components. The radioprotective coating agent can be used, for example, as a coating agent for films and sheets for which radioprotective measures are necessary; walls and interior materials of radiation facilities; radioprotective glasses or radioprotective contact lenses; clothes linings for people who are likely to be exposed to radiation, such as pilots, flight attendants, astronauts, radiation facility workers; and various other products.

The radioprotective cosmetic product can be produced, for example, by adding the radioprotective material as it is or as bonded to or immobilized on particles (beads), to cosmetic components and thereby mixing the material with the cosmetic components. The cosmetic product thus obtained is useful as a radioprotection measure for people who are likely to be exposed to radiation (for example, astronauts, military personnel, pilots, flight attendants, radiological technologists, nuclear power plant workers, radiation facility workers, people who live near radiation facilities, etc.). Moreover, the cosmetic product can be used as a radiation (ultraviolet rays)-blocking cosmetic product that protects the exposed skin of the face, hand, etc. from various types of radiation (Ultraviolet-A, Ultraviolet-C, alpha rays and beta rays) emanated from the atmosphere, electronic or electrical equipment, or the like. Therefore, the cosmetic product can also be used as a radioprotection measure for people in normal living environments.

The radioprotective fiber can be prepared, for example, by kneading the radioprotective material directly into fiber (spinning raw material), or coating, adhering or bonding the material onto the surface of fiber. Since the radioprotective fiber thus obtained blocks or reduces the effects of various types of radiation emanated from the atmosphere, the earth's surface, electronic and electrical equipment, etc., it can be used, for example, for the linings of space suits; underwear, gloves and other clothing for pilots, flight attendants, radiation facility workers, etc.; curtains for radiation facilities; and interior materials of radiation facilties, spacecraft, aircraft, etc.

The radioprotective preparation is used for reducing the adverse effects of radiation on non-affected parts in radiotherapy or radiographic inspection to thereby protect the body. The form of preparation is not limited, and can be suitably selected depending on the intended use from external, non-oral, oral and other forms. The radioprotective preparation is produced, for example, by formulating the radioprotective material, singly or in combination with conventional pharmaceutical carriers, into a preparation such as an external preparation (cream, ointment, patches or the like), a non-oral preparation (injection, suppositories, enteric preparation or the like) or an oral preparation, in the standard manner.

Further, the radioprotective material and radioprotective product can be used as radiation-resistant medical or experimental material. The radiation-resistant medical or experimental material is a material for use in medical applications or experiments that inhibits functional deterioration due to the actions of radiation emitted by radiation sterilization or the like. As used herein, medical or experimental materials include not only non-biological materials such as various pharmaceutical components, medical devices and laboratory instruments, but also biological materials such as enzymes, cells and biological tissues. The radiation-resistant medical or experimental material of the present invention can be prepared using the radioprotective material or radioprotective product of the present invention, for example, by mixing the radioprotective material with a non-biological or biological material; or by immobilizing the radioprotective material on a non-biological or biological material; or by covering a non-biological or biological material with the radioprotective product in the form of, for example, a coating agent, sheet or film.

(II) Method for Blocking or Reducing the Adverse Effects of Radiation

As mentioned above, collagens, keratins, silk fibroins and their derivatives are capable of blocking or reducing the adverse effects of radiation on a subject. Thus, the present invention also provides a method for blocking or reducing the adverse effects of radiation on a subject, the method comprising using at least one member selected from the group consisting of collagens, keratins, silk fibroins and their derivatives to protect the subject.

In the method of the present invention, the radiation to be blocked or reduced are the same as for the radioprotective material.

Moreover, in the method of the present invention, usable collagens, keratins, silk fibroins and derivatives thereof are the same as for the radioprotective material.

In the method of the present invention, the subject to be protected is not limited as long as it needs protection from the adverse effects of radiation. Examples of such subjects include agricultural products, marine products, foods, domestic animals, pets, humans, electronic precision instruments, textiles, medical or experimental materials, etc.

In the method of the present invention, the process of using collagens, keratins, silk fibroins or their derivatives on the subject is not limited as long as they are used so as to be present inside or on the surface of the subject. As used herein, the expression "be present on the surface of the subject" does not necessarily mean adhering to the surface of the subject.

Specific embodiments of the method of the present invention include using (e.g., administering, mixing, coating or immobilizing), to protect the subject, a collagen, keratin, silk fibroin or derivative thereof singly, or a composition comprising any of these components (active ingredients) and a base material, carrier or additive. Other specific embodiments of the method include placing (e.g., covering, coating or fitting) a product (e.g., coating agent, film, sheet, cosmetic product, fiber, external preparation, non-oral preparation or oral preparation) comprising a collagen, keratin, silk fibroin or derivative thereof over the subject; applying the product to the subject; and administering (e.g., externally administering, internally administering, injecting or ingesting) the product to the subject.

In any of the above embodiments, it is desirable that the collagen, keratin, silk fibroin or derivative thereof be used in such a proportion that the subject has 0.05 wt. % to 40 wt. %, preferably about 1 wt. % to about 10 wt. % in total of these components inside the subject or inside a surface layer of the subject. However, the preferred proportion may vary depending on the type of subject, expected results and the like, and therefore is not limited to the above. When the proportion of these components is markedly lower than 0.05 wt. %, the capability of blocking or reducing the adverse effects of radiation is likely to be low. These components, when contained in a proportion higher than 40 wt. %, have no bad influence on the effects of the present invention. Therefore, these components may be contained in a proportion higher than 40 wt. % as long as they do not adversely influence the functions and shape of the subject.

(III) Use of at Least One Member Selected from the Group Consisting of Collagens, Keratins, Silk Fibroins and their Derivatives As stated above, collagens, keratins, silk fibroins and their derivatives are capable of blocking or reducing the adverse effects of radiation. Accordingly, the present invention further provides use of at least one member selected from the group consisting of collagens, keratins, silk fibroins and their derivatives as a radioprotective material; use of at least one member selected from the group consisting of collagens, keratins, silk fibroins and their derivatives for production of a radioprotective material; and use of at least one member of selected from the group consisting of collagens, keratins, silk fibroins and their derivatives for production of a radioprotective product. The collagens, keratins, silk fibroins and derivatives to be used, and the modes of using these substances are as described above.

EXAMPLES

The following Examples and Experiments are provided to illustrate the present invention in further detail and are not intended to limit the scope of the invention. Unless otherwise specified, the proteins used in the following Examples and Experiments are: a collagen (tradename COLLA, manufactured by Nitta Gelatin Inc.), a collagen derivative (a cationized collagen, tradename PROMOIS W-42CAQ, manufactured by Seiwa Kasei Co., Ltd.), a keratin (tradename HUMAN EPITHELIUM, manufactured by Pharmaceuticals, Inc.), a keratin derivative (a cationized keratin, tradename PROMOIS W-WH-HO, manufactured by Seiwa Kasei Inc.), a silk fibroin (tradename FIBROIN POWDER, manufactured by Daiwabo Co., Ltd.), a silk fibroin derivative [cocodimonium hydroxypropyl silk amino acids, MW3500, tradename CROSILKQUAT, manufactured by Croda Inc.], a silk sericin (tradename SERICIN POWDER, manufactured by Serene), a milk casein (tradename HAMMERSTEIN, manufactured by Merck Co., Ltd.), a milk casein derivative (N,N-dimethylated casein, manufactured by Cabiochem-Novabiochem Corp.), a soybean casein (tradename FUJIPRO AL, manufactured by Fujipurina Protein), a soybean casein derivative (hydroxy-3(lauryldimethylammonio)propyl chloride hydrolysate MW5500, tradename CROWAT SOYA, manufactured by Croda Inc.), a wheat protein derivative (hydroxy-3(trimethylammonio) propyl chloride hydrolysate, MW5000, tradename HYDROTRITICOM WQ, manufactured by Croda Inc.).

Example 1

Radioprotective Plastic Product (Sheet)

A resin composition was prepared by mixing, at 60° C. in a twin-screw mixer, 62.5 parts by weight of a polylactic acid resin (tradename ECOPLA, average molecular weight 8800, L/D: 98.5/1.5, manufactured by Cargil-Dow), 20.8 parts by weight of a fatty acid polyester (tradename BIONOLLE 101, manufactured by Showa High Polymer Co., Ltd.) and 16.7 parts by weight of silk fibroin. The obtained resin composition was extruded from a T-die extruder at an extrusion temperature of 160° C., and cooled at a die temperature of 60° C. to prepare a radioprotective plastic product (sheet) with a size of 1 mm (thickness)×180 mm×10 m. The sheet had a tear strength of 10.2 kgf (measured according to JIS K-6732).

Example 2

Radioprotective Plastic Product (Sheet)

The procedure of Example 1 was followed except for using the same amount of collagen or keratin in place of the silk fibroin to prepare a radioprotective plastic product (sheet). The obtained radioprotective plastic product (sheet) had an excellent tear strength.

Example 3

Radioprotective Plastic Product (Film)

A resin composition was prepared by mixing, at 60° C. in a twin-screw mixer, 62.5 parts by weight of a polylactic acid resin (tradename ECOPLA, an average molecular weight 8800, L/D: 98.5/1.5, manufactured by Cargil-Dow), 20.8 parts by weight of a fatty acid polyester (tradename BIONOLLE 101, manufactured by Showa High Polymer Co., Ltd.), and 16.7 parts by weight of collagen. The obtained resin composition was subjected to rotation extrusion using an inflation extruder at a rotational speed of 220 rpm, to prepare a radioprotective plastic product (film) with a size of 0.08 mm (thickness)×900 mm×10 m. The film had a tear strength of 2.25 kgf (measured according to JIS K-6732).

Example 4

Radioprotective Plastic Product (Film)

The procedure of Example 3 was followed except for using the same amount of silk fibroin or keratin in place of the collagen, to prepare a radioprotective plastic product (film). The obtained radioprotective plastic product (film) had an excellent tear strength.

Example 5

Radioprotective Film

Twenty grams of collagen, whose average molecular weight had been adjusted to 250,000, was added to 80 ml of 50° C. warm water and mixed in a homomixer to form a suspension. The suspension was spread thinly over a plate and dried at 105° C. by evaporating the moisture, thereby preparing a radioprotective film.

Example 6

Radioprotective Film

The procedure of Example 5 was followed except for using the same amount of silk fibroin or keratin each having an average molecular weight of 200,000 to 3,000,000 in place of the collagen, to prepare a radioprotective film.

Example 7

Radioprotective Sheet

Purified water was uniformly sprayed on the surface of the radioprotective film obtained in Example 5 or 6 to such an extent that no water drops remained. Ten such films were laminated. The laminate was compressed and then dried by heating at 105° C. to adhere the films with one another, thereby giving a radioprotective sheet.

Example 8

Radioprotective Coating Agent

One kilogram of silk fibroin, 5 g of polyethylene glycol 300 (polysorbate 80) and 250 g of methacrylic acid copolymer LD (manufactured by Eudragit) were added to 15 L of water, followed by mixing, to prepare a radioprotective coating agent.

Example 9

Radioprotective Coating Agent

The procedure of Example 8 was followed except for using the same amount of collagen or keratin in place of the silk fibroin, to prepare a radioprotective coating agent.

Example 10

Radioprotective Cosmetic (Cream)

Into a 1 L stainless steel container were sequentially added 5.8 parts by weight of polyoxyethylene oleyl ether phosphoric acid (tradename CRODAPHOS, manufactured by Croda Inc.), 2.5 parts by weight of cetostearyl alcohol (tradename CRODACOHOL S, manufactured by Croda Inc.), 7.1 parts by weight of high-purity vaseline (tradename SUN WHITE P-200, manufactured by Nikko Rica Corp.), 11.6 parts by weight of liquid paraffin (manufactured by Wako Pure Chemical Ind. Ltd.), 0.4 parts by weight of poly(2)oxyethylene stearyl ether (tradename NIKKOL BS-2, manufactured by Nikko Chemical Co., Ltd.), 2.1 parts by weight of poly(10)oxyethylene stearyl ether (tradename NIKKOL BC-10EX, manufactured by Nikko Chemical Co., Ltd.), 4.6 parts by weight of liquid lanolin (tradename FULLIRAN SP, manufactured by Croda Inc.), 1.7 parts by weight of propylene glycol (manufactured by Wako Pure Chemical Ind. Ltd.), 0.2 parts by weight of triethanolamine, 55.7 parts by weight of purified water and 8.3 parts by weight of silk fibroin. The resulting mixture was stirred in a homomixer at 250 rpm, thereby giving a radioprotective cosmetic product (cream).

Example 11

Radioprotective Cosmetic Product (Cream)

The procedure of Example 11 was followed except for using the same amount of collagen or keratin in place of the silk fibroin, to prepare a radioprotective cosmetic product (cream).

Example 12

Radioprotective Fiber

In a twin-screw mixer, 62.5 parts by weight of a polylactic acid resin (tradename ECOPLA, average molecular weight 8800, L/D: 98.5/1.5, manufactured by Cargil-Dow), 20.8 parts by weight of a fatty acid polyester (tradename BIONOLLE 101, manufactured by Showa High Polymer Co., Ltd.) and 16.7 parts by weight of keratin were mixed at 60° C. to prepare a spinning material composition. The obtained spinning material composition was dried by heating at 105° C. for 12 hours. Subsequently, using a pressure melter type spinning machine, the dry composition was melted at 180° C. and spun at a spinning temperature of 180° C., thereby giving a radioprotective fiber.

Example 13

Radioprotective Fiber

The procedure of Example 12 was followed except for using the same amount of collagen or silk fibroin in place of the keratin, to prepare a radioprotective fiber.

Example 14

Radioprotective Fiber

Fifty grams of the coating agent prepared in Example 8 was added, dispersed and dissolved into 100 ml of water. The obtained solution was warmed to 70° C., sprayed on a fiber (100% cotton) in an amount of 240 parts by weight relative to 100 parts by weight of the fiber and dried at 105° C., thereby giving a radioprotective fiber.

Example 15

Radioprotective Fiber

The procedure of Example 14 was followed except for using the same amount of the coating agent of Example 9 in place of the coating agent of Example 8, to prepare a radioprotective fiber.

Example 16

Radioprotective Fiber

One hundred parts by weight of water, 2 parts by weight of the coating agent prepared in Example 8, and 10 parts by weight of fiber (100% cotton) were placed into a washer dyeing machine and treated at 60° C. for 2 hours. The fiber was then taken out and dried at 105° C., thereby giving a radioprotective fiber.

Example 17

Radioprotective Fiber

The procedure of Example 16 was followed except for using the same amount of the coating agent of Example 9 in place of the coating agent of Example 8 to prepare a radioprotective fiber.

Experiment 1

A collagen, keratin or silk fibroin was added to aqueous solutions containing 1 ml of a-amylase (C•P•R Co. Ltd., enzyme activity: 8,000 U/ml) to give final concentrations of 2 wt. % and 10 wt. %. The resulting solutions were irradiated with gamma rays (10 kGy). The residual a-amylase activity of the irradiated solutions was measured to find the residual amount (%) of a-amylase activity. For comparison, the same procedure was repeated using silk sericin, milk casein, soy casein, wheat protein or albumin in place of the collagen, keratin or silk fibroin, and the residual amount (%) of a-amylase activity was measured.

The measurement of a-amylase activity was carried out in the following manner: 1 ml of each of the gamma ray-irradiated enzyme solutions, suitably diluted, was separately added to 20 ml of a 1 wt. % potato starch solution, followed by reaction at 40° C. The end of the reaction was detected by monitoring reactions with an iodine solution, taking the time at which iodine-starch reaction became negative as the end of the reaction. From the time required until the end of the reaction, the enzyme activity was calculated according to the following equation:

$$\text{Enzyme Activity} = 200 \times \frac{\text{Dilution ratio of gamma ray-irradiated enzyme solution}}{\text{Time required until the end of reaction}}$$

The residual proportion (%) of a-amylase activity was calculated by comparison of the enzyme activity found above with the enzyme activity before gamma ray irradiation.

Table 1 shows the results.

TABLE 1

| Protein concentration | Residual proportion of a-amylase activity (%) | |
|---|---|---|
| | 2 wt. % | 10 wt. % |
| Collagen | 2.67 | 18.80 |
| Keratin | 2.01 | 20.10 |
| Silk fibroin | 1.70 | 5.60 |
| Silk sericin | 0.12 | 0.40 |
| Milk casein | 0.05 | 0.30 |
| Soy casein | 0.01 | 0.15 |
| Wheat protein | 0.00 | 0.01 |
| Albumin | 0.00 | 0.05 |
| No protein | 0.00 | 0.00 |

The results reveal that the collagen, keratin and silk fibroin significantly inhibit the a-amylase activity reduction caused by gamma ray irradiation as compared with other proteins, demonstrating that the collagen, keratin and silk fibroin have a high protective effect against gamma rays. Therefore, collagens, keratins and silk fibroins are useful as radioprotective materials that reduce the effects of radiation (gamma rays).

Experiment 2

A collagen, keratin or silk fibroin was added to aqueous solutions containing 1 ml of a-amylase (C•P•R Co. Ltd., enzyme activity: 8,000 U/ml) to give a final concentration of 2.5 wt. %. The resulting solutions were irradiated with UV rays for periods ranging from 0 to 5 hours, and the residual a-amylase activity of the irradiated solutions was then measured. As control experiments, UV irradiation was performed in the same manner as above on a-amylase solutions containing silk sericin, milk casein, soy casein, wheat protein or albumin, and on an a-amylase solution containing no protein, to measure the residual a-amylase activity.

Specifically, the measurement was carried out in the following manner: First, 0.2 ml of a solution containing a-amylase and one of the proteins was applied to the upper surface of a glass slide, dried at room temperature, and irradiated with an ultraviolet lamp (15 W) from 15 cm above the upper surface of the slide glass. After irradiation, the dried enzyme solution on the slide glass was dissolved in 0.2 ml of distilled water, and the a-amylase activity of the resulting solution was measured in the same manner as in Experiment 1. The residual proportion (%) of a-amylase activity was calculated by comparing the a-amylase activity measured above with the enzyme activity before the UV irradiation. Table 2 shows the results.

TABLE 2

| UV irradiation time | Residual proportion of a-amylase activity (%) | | |
|---|---|---|---|
| | 0 hour | 1 hour | 5 hours |
| Collagen | 100.0 | 100.0 | 100.0 |
| Keratin | 100.0 | 100.0 | 100.0 |
| Silk fibroin | 100.0 | 100.0 | 98.1 |
| Silk sericin | 100.0 | 87.0 | 71.0 |
| Milk casein | 100.0 | 81.1 | 66.7 |
| Soy casein | 100.0 | 79.2 | 65.0 |
| Wheat protein | 100.0 | 80.0 | 62.8 |
| Albumin | 100.0 | 75.0 | 59.9 |
| No protein | 100.0 | 80.6 | 64.0 |

The results reveal that when collagen, keratin or silk fibroin was used as a radioprotective material, the a-amylase activity was scarcely reduced by UV irradiation, demonstrating that collagen, keratin and silk fibroin have a remarkably high protective effect against UV irradiation. Therefore, collagens, keratins and silk fibroins are useful as radioprotective materials that reduce the effects of radiation (UV rays).

Experiment 3

Collagen, keratin or silk fibroin was added to aqueous solutions containing 1 ml of a-amylase (C•P•R Co. Ltd., enzyme activity: 8,000 U/ml) to give a final concentration of 1.25 wt. %. Using the resulting solutions, glass slide samples were prepared in the same manner as in Experiment 2, and irradiated with X-rays (10 kGy), electron beams (10 kGy) or gamma rays. The residual a-amylase activity was then measured and the residual proportion (%) of a-amylase activity was found in the same manner as in Experiment 1. As control experiments, irradiation was performed in the same manner as above on a-amylase solutions containing silk sericin, milk casein, soy casein, wheat protein or albumin, and on an a-amylase solution containing no protein, to measure the residual a-amylase activity and find the residual proportion (%) of a-amylase activity. Table 3 shows the results.

TABLE 3

| Type of radiation | Residual proportion of a-amylase activity (%) | | | |
|---|---|---|---|---|
| | No radiation | X-rays | Electron beams | Gamma rays |
| Collagen | 100.0 | 98.6 | 99.6 | 82.6 |
| Keratin | 100.0 | 84.7 | 98.8 | 90.9 |
| Silk fibroin | 100.0 | 90.6 | 93.2 | 88.6 |
| Silk sericin | 99.8 | 22.1 | 24.5 | 15.1 |
| Milk casein | 99.7 | 66.8 | 56.7 | 18.8 |
| Soy casein | 100.0 | 43.2 | 31.1 | 11.1 |
| Wheat protein | 100.0 | 51.8 | 28.9 | 12.4 |
| Albumin | 99.7 | 24.8 | 41.8 | 11.1 |
| No protein | 100.0 | 22.8 | 38.4 | 11.0 |

The results reveal that collagen, keratin and silk fibroin minimize the a-amylase activity reduction caused by irradiation with gamma rays or electron beams, demonstrating that collagen, keratin and silk fibroin have an extremely high protective effect against these radiation sources. Therefore, collagens, keratins and silk fibroins are useful as radioprotective materials that reduce the effects of radiation (X-rays, electron beams and gamma rays).

Experiment 4

Using a-amylase solutions containing a collagen derivative, keratin derivative or silk fibroin derivative at a final concentration of 1.25 wt. %, glass slide samples were prepared in the same manner as in Experiment 2. The samples were irradiated with X-rays (10 kGy), electron beams (10 kGy) or gamma rays (10 kGy). The residual a-amylase activity was then measured and the residual proportion (%) of a-amylase activity was found in the same manner as in Experiment 1. For comparison, the same procedure as above was followed using a wheat protein derivative, milk casein derivative or soy casein derivative in place of the collagen derivative, keratin derivative or silk fibroin derivative. Table 4 shows the results.

TABLE 4

| Type of radiation | Residual proportion of a-amylase activity (%) | | | |
| --- | --- | --- | --- | --- |
| | No radiation | X-rays | Electron beams | Gamma rays |
| Collagen derivative | 100.0 | 99.6 | 90.4 | 88.1 |
| Keratin derivative | 98.0 | 98.1 | 78.9 | 65.4 |
| Silk fibroin derivative | 100.0 | 97.6 | 88.6 | 32.8 |
| Wheat protein derivative | 99.8 | 54.8 | 40.0 | 6.5 |
| Milk casein derivative | 98.6 | 43.6 | 27.8 | 7.4 |
| Soy casein derivative | 99.0 | 18.6 | 12.8 | 5.2 |
| No protein | 100.0 | 15.0 | 8.0 | 4.6 |

The results reveal that, as with collagen, keratin and silk fibroin, the collagen derivative, keratin derivative and silk fibroin derivative have an extremely high protective effect against X-rays, electron beams and gamma rays. Therefore, collagen derivatives, keratin derivatives and silk fibroin derivatives are useful as radioprotective materials that reduce the effects of radiation (X-rays, electron beams and gamma rays).

INDUSTRIAL APPLICABILITY

The radioprotective material of the present invention blocks the effects of various types of radiation, and therefore is capable of significantly preventing radiation exposure in nuclear power facilities, medical facilities, aircraft in flight, uranium ore refineries, and construction sites where radiography is used. Moreover, the material of the invention is capable of protecting organisms and articles such as precision equipment, photographic dry plates or the like from damage caused by radiation emitted from experimental equipment, color televisions or like electrical appliances containing radiation tubes, or by radiation from outer space or the earth's crust. Further, the radioprotective material of the invention, which is derived from naturally occurring substances, is valuable from the viewpoint of environmental conservation.

Furthermore, the method of the invention can effectively block or reduce the adverse effects of radiation on a subject, and thus can prevent the functional deterioration of or damage to the subject by radiation.

The invention claimed is:

1. A method for blocking or reducing the adverse effects on a medical or experimental material when the medical or experimental material is exposed to 10 kGy or more of at least one type of radiation selected from the group consisting of x-rays, gamma rays and electron beams, the method comprising:
    covering the medical or experimental material in need of protection from said adverse effects with a sheet or film comprising at least one member selected from the group consisting of keratins, silk fibroins and their derivatives.

2. A method according to claim 1, wherein the sheet or film comprises at least one member selected from the group consisting of keratins, silk fibroins and their derivatives in a total amount of 0.05 wt. % to 40 wt. % based on the weight of the sheet or film.

3. The method of claim 1, wherein the medical or experimental material is exposed to 10 kGy or more radiation over the course of 0-5 hours.

* * * * *